United States Patent
Forthmann et al.

(10) Patent No.: US 10,894,174 B2
(45) Date of Patent: Jan. 19, 2021

(54) ROTATABLE MAGNET FOR PROTON THERAPY

(71) Applicant: KONINKLIJKE PHILIPS N.V., Eindhoven (NL)

(72) Inventors: Peter Forthmann, Eindhoven (NL); Philip Alexander Jonas, Eindhoven (NL); Johannes Adrianus Overweg, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 213 days.

(21) Appl. No.: 15/777,929

(22) PCT Filed: Dec. 1, 2016

(86) PCT No.: PCT/EP2016/079496
§ 371 (c)(1),
(2) Date: May 22, 2018

(87) PCT Pub. No.: WO2017/093434
PCT Pub. Date: Jun. 8, 2017

(65) Prior Publication Data
US 2018/0318608 A1 Nov. 8, 2018

Related U.S. Application Data

(60) Provisional application No. 62/261,893, filed on Dec. 2, 2015.

(51) Int. Cl.
*A61N 5/10* (2006.01)
*G01R 33/38* (2006.01)
(Continued)

(52) U.S. Cl.
CPC ............ *A61N 5/1049* (2013.01); *A61B 5/055* (2013.01); *G01R 33/3804* (2013.01);
(Continued)

(58) Field of Classification Search
CPC .......... A61N 5/1049; A61N 2005/1055; A61N 2005/1087; G01R 33/3804; G01R 33/3815; G01R 33/4808; A61B 5/055
See application file for complete search history.

(56) References Cited

U.S. PATENT DOCUMENTS 4,796,433 A * 1/1989 Bartlett ..................... H01F 6/04
62/47.1
5,168,211 A 12/1992 Laukien et al.
(Continued)

FOREIGN PATENT DOCUMENTS

| EP | 1464976 A2 | 10/2004 |
| EP | 2637181 A1 | 9/2013 |

*Primary Examiner* — Dixomara Vargas

(57) ABSTRACT

The following relates generally to use of magnetic resonance (MR) imaging as guidance in radiation therapy, and more specifically to use of MR imaging as guidance in proton therapy. In some embodiments, a cryogenic dewar is provided with multiple channels allowing a proton beam from a proton beam source to pass through. The proton beam may first be aligned with a first channel, and the dewar may then be rotated along with the proton source. The dewar may then be rotated to align a second channel with the proton beam.

19 Claims, 3 Drawing Sheets

(51) Int. Cl.
  *G01R 33/3815*  (2006.01)
  *G01R 33/48*  (2006.01)
  *A61B 5/055*  (2006.01)

(52) U.S. Cl.
  CPC ..... *G01R 33/3815* (2013.01); *G01R 33/4808* (2013.01); *A61N 2005/1055* (2013.01); *A61N 2005/1087* (2013.01)

(56) References Cited

U.S. PATENT DOCUMENTS

| | | | |
|---|---|---|---|
| 5,482,919 A * | 1/1996 | Joshi | H02K 55/04 310/52 |
| 7,489,131 B2 * | 2/2009 | Lvovsky | G01R 33/3856 324/300 |
| 8,204,562 B2 * | 6/2012 | Kwon | H02K 55/06 505/166 |
| 8,427,148 B2 | 4/2013 | O'Connor | |
| 8,525,116 B2 * | 9/2013 | Schulz | G01T 1/1603 250/363.02 |
| 8,788,016 B2 | 7/2014 | Roell et al. | |
| 9,293,253 B2 * | 3/2016 | Calvert | G01R 33/3815 |
| 9,543,066 B2 * | 1/2017 | Calvert | H01F 6/06 |
| 2008/0259560 A1 * | 10/2008 | Lvovsky | G01R 33/3856 361/689 |
| 2009/0038318 A1 * | 2/2009 | Begg | H01F 6/04 62/47.1 |
| 2009/0093369 A1 * | 4/2009 | Kwon | H02K 55/06 505/166 |
| 2010/0219347 A1 * | 9/2010 | Schulz | G01T 1/1603 250/363.04 |
| 2011/0156703 A1 | 6/2011 | O'Connor | |
| 2011/0196226 A1 | 8/2011 | Gross et al. | |
| 2013/0225974 A1 | 8/2013 | Van Den Brink | |
| 2014/0128719 A1 | 5/2014 | Longfield | |
| 2014/0135615 A1 | 5/2014 | Kruip | |
| 2014/0163664 A1 * | 6/2014 | Goldsmith | A61B 17/12181 623/1.11 |
| 2014/0266208 A1 | 9/2014 | Dempsey et al. | |
| 2014/0274722 A1 * | 9/2014 | Calvert | H01F 6/06 505/163 |
| 2016/0172089 A1 * | 6/2016 | Calvert | H01F 41/048 335/216 |
| 2017/0120075 A1 * | 5/2017 | Overweg | A61N 5/1081 |

\* cited by examiner

ROTATABLE MAGNET FOR PROTON THERAPY

CROSS REFERENCE TO RELATED APPLICATIONS

This application is a U.S. national phase application of International Application No. PCT/EP2016/079496, filed on Dec. 1, 2016, which claims the benefit of U.S. provisional Application Ser. No. 62/261,893 filed on Dec. 2, 2015 and is incorporated herein by reference.

BACKGROUND

The following relates generally to use of magnetic resonance (MR) imaging as guidance in radiation therapy, MR imaging as guidance in proton therapy, and the like.

In tomographic x-ray radiation therapy, magnetic resonance (MR) imaging is sometimes used to provide image guidance for the therapy procedure. Interposing the MR imaging device produces a large (e.g. ~40%) loss in x-ray beam intensity, with the potential for some x-ray scattering.

Currently, proton therapy is typically performed without monitoring by imaging of any modality. Real-time image monitoring of proton therapy could serve various purposes such as assisting in positioning the tumor in the therapy system, detecting and possibly correcting for patient motion due to breathing, performing session specific therapy plan adjustments, documenting the therapy session, or so forth. MR imaging is particularly well-suited for this as it can provide soft tissue contrast enabling imaging of the tumor and neighboring critical structures. However, the proton beam is even more strongly affected by the interposed MR device than an x-ray beam, as the proton beam cannot penetrate the cryoshroud of a superconducting MR magnet and is also deflected by the magnetic field.

The following provides a new and improved systems and methods which overcome the above-referenced problems and others.

SUMMARY

In one aspect, a horizontal bore magnet having a cylinder axis includes: a cryogenic dewar having an outer cylindrical wall and an inner cylindrical wall arranged coaxially respective to the cylinder axis and a cryogenic fluid plenum defined between the outer and inner cylindrical walls, the inner cylindrical wall surrounding a magnet bore; annular magnet windings disposed in the cryogenic fluid plenum; and at least one radial channel having an outer end sealed with the outer cylindrical wall of the cryogenic dewar and an inner end sealed with the inner cylindrical wall of the cryogenic dewar, the at least one channel passing radially through the dewar. The at least one radial channel may include a plurality of radial channels passing radially through the dewar. The the radial channels may be curved to account for a $\bar{q}\bar{v}\times\bar{B}$ force deflecting a proton beam passing through the channel. The cryogenic dewar may be a liquid helium dewar, the cryogenic fluid plenum may be a liquid helium plenum, and the annular magnet windings may be superconducting magnet windings. The channels may be air-filled. The channels may be evacuated of air. The channels may be filled with a gas that has a density less than air, and the channels may be sealed. The horizontal bore magnet may further include a mechanical rotation system comprising a motor arranged to rotate the dewar about the cylinder axis over an angle of at least 360°/N where N is the number of channels.

The annular magnet windings may be secured with the cryogenic dewar as a unit and the mechanical rotation system rotates the annular magnet windings and the cryogenic dewar as a unit; alternatively, the annular magnet windings may be supported separately from the cryogenic dewar and the mechanical rotation system rotates the cryogenic dewar while the annular magnet windings remain stationary. A cosine function may be used to smooth a stopping of rotation of the dewar.

In another aspect, a magnetic resonance (MR) imaging system includes: a horizontal bore magnet including a cryogenic dewar having multiple channels passing through the dewar towards a cylinder axis of the cryogenic dewar. The MR imaging system may further include a mechanical rotation system configured to rotate the dewar. The mechanical rotation system may be programmed to control rotation of the dewar such that the dewar rotates synchronously with a proton beam tomographically revolving around the cylinder axis. The channels may be curved in accordance with a $\bar{q}\bar{v}\times\bar{B}$ force on protons. The channels may be air-filled channels. The channels may be filled with a gas that has a density less than air, and the channels may be sealed.

In another aspect, a method of magnetic resonance (MR) imaging may be performed in conjunction with an MR device including magnet windings generating a magnetic field for MR imaging and a cryogenic dewar containing the magnet windings, the cryogenic dewar including at least one channel passing radially through the cryogenic dewar; the method including: during a first rotation, rotating, in a first direction, the cryogenic dewar while a proton beam passes through a first channel of the cryogenic dewar towards a center axis of the dewar. The method may further include during a second rotation performed after completing the first rotation, rotating, in a second direction opposite to the first direction, the cryogenic dewar to align a second channel of the dewar with the proton beam. The method may further include that the magnetic windings are secured with the cryogenic dewar such that the rotating rotates the cryogenic dewar and the magnetic windings together as a unit. The method may further include that the first rotating is performed in a step-and-shoot operation in which the proton beam is stepped in increments with an irradiation scan performed at each incremental angular position.

One advantage resides in a better targeting of radiation therapy.

Another advantage resides an MRI system having a better uniformity of a magnetic field.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

DETAILED DESCRIPTION

To solve the problem of radiation absorption in an MR imaging device used to monitor radiation therapy, the disclosed approach provides several channels through the cryogenic (e.g. liquid helium, LHe) dewar providing cooling of the magnet. This approach leverages the recognition herein that the magnet windings either do not include central winding sections at the central plane of the magnet, or if central winding sections are present they are spaced apart around the bore with relatively large gaps, e.g. typically of at least 10 cm between adjacent sections. In embodiments disclosed herein, channels are added passing through the cryogenic dewar. These channels can be added without modifying the magnetic coil layout design, or with only minimal modifications such as adding shims to compensate for any magnetic field distortion introduced by the air-filled channels passing through the cryogenic cooling medium.

In illustrative embodiments disclosed herein, proton therapy is considered as the radiation therapy modality. However, it will be appreciated that the disclosed approaches are amenable for use with other types of radiation therapy, such as x-ray radiation therapy or heavy ion therapy where the disclosed channels can reduce or eliminate radiation losses and/or scattering in the intervening MR imaging device. In the illustrative embodiments the magnet is a horizontal bore superconducting magnet cooled by a liquid helium (LHe) dewar, but in other embodiments the cryogenic fluid may be another type of coolant.

In one embodiment, the channels have small cross-section, which is advantageous for eliminating or minimizing impact on the magnet performance. In such embodiments, to obtain 360° angular coverage for the proton beam, the LHe dewar is rotated about its horizontal axis. For example, if there are eight channels spaced apart at 360°/8=45° intervals around the bore, then the proton therapy could be performed as follows: align the proton beam with the first channel, perform a 45° arc of radiation therapy angular steps while rotating the LHe dewar between each angular step in sync with the angular beam movement, then shutter the proton beam and rotate the dewar back to its starting position thus aligning the beam with the second channel, and repeat so as to successively cover 45°×8=360°.

Figure 1:
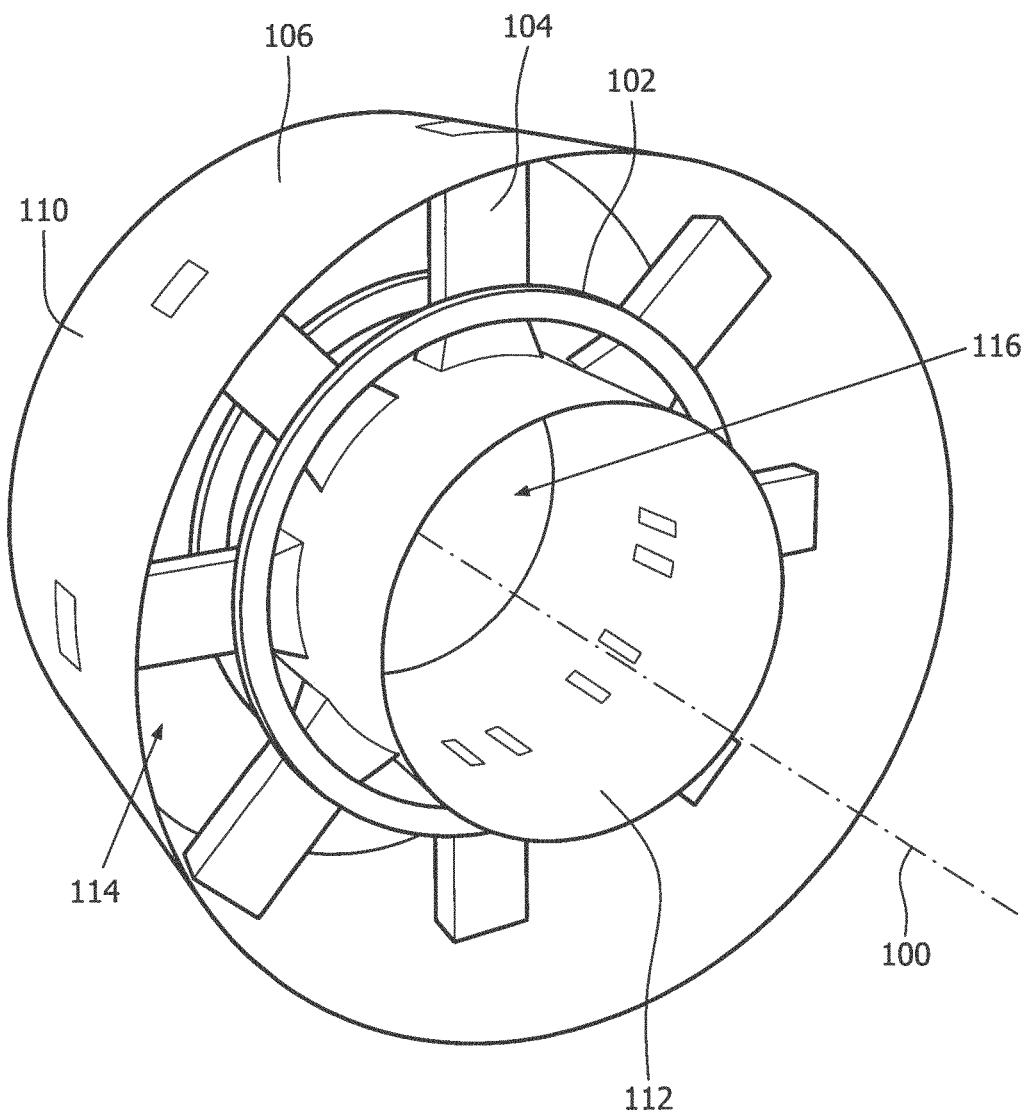
FIG. 1 illustrates an embodiment with eight channels.
Figure 2:
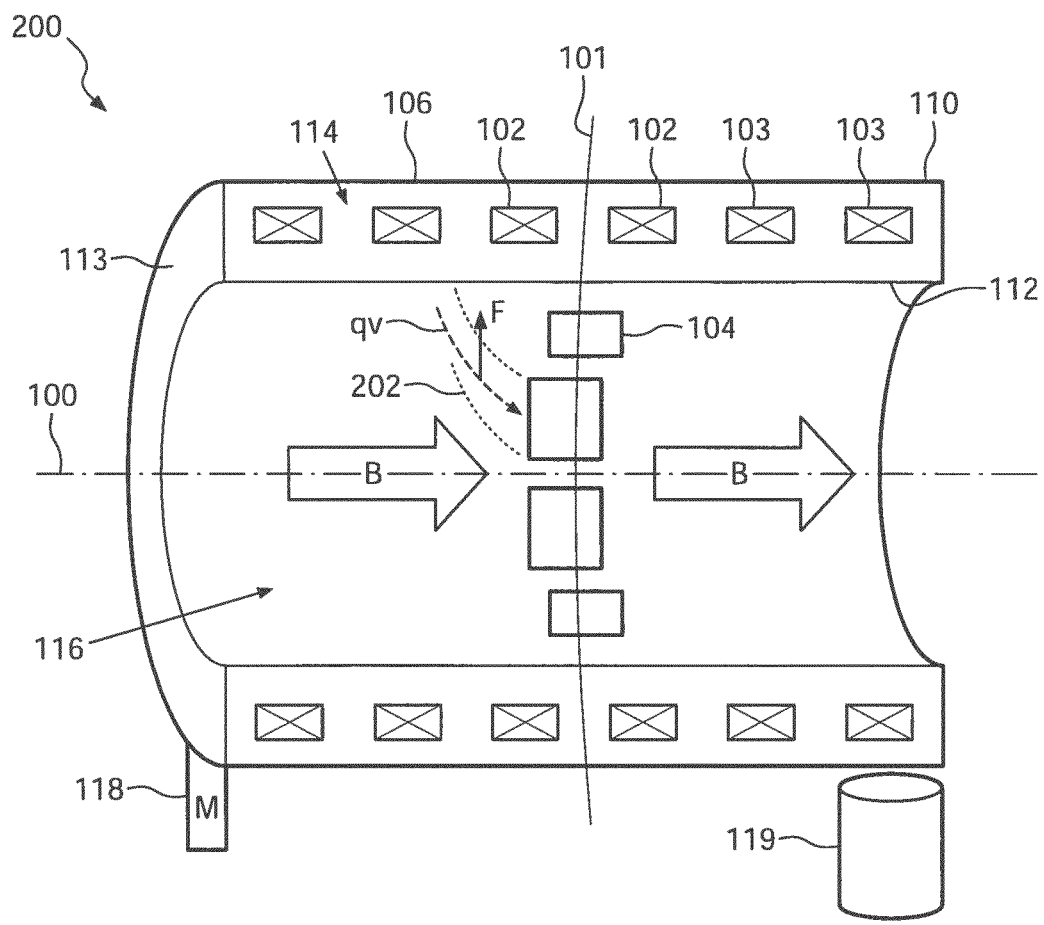
FIG. 2 illustrates an embodiment of a cross section of a gantry.

FIGS. 1 and 2 illustrate a central portion of a horizontal bore magnet design in accordance with this illustrative eight channel approach. With reference thereto, the horizontal bore of the magnet is indicated as cylinder axis 100, along with a central plane 101 of the magnet (indicated only in FIG. 2). The horizontal bore magnet is typically rotationally symmetric about the cylinder axis 100 and bilaterally symmetric about the central plane 101. In FIG. 1, annular magnetic winding sections 102, 103, channels 104, and a LHe dewar 106 are shown. Only the two most central magnet winding sections 102 are shown in FIG. 1, but as shown in FIG. 2 the magnet may include additional winding sections 103 positioned further away from the central plane 101 of the magnet. The cryogenic dewar 106 includes an outer cylindrical wall 110 and an inner cylindrical wall 112 sealed at their ends by end-walls 113 (one seen in FIG. 2). A cylindrical LHe plenum 114 is defined between these walls 110, 112, 113. The superconducting magnet windings 102, 103 are disposed in the LHe plenum 114, which is (mostly) filled with liquid helium so that the superconducting magnet windings 102, 103 are immersed in the liquid helium to maintain the windings 102, 103 at a temperature below the superconducting transition temperature for the winding material at the operating electrical current. Although not shown in diagrammatic FIG. 1, the cylindrical walls 110, 112 may include additional thermal isolation structure, such as one or more cylindrical plenums defining liquid nitrogen and/or vacuum jacketing in accord with conventional cryogenic dewar design, and likewise for the end-walls 113.

The radially oriented channels 104 contain air inside, and the outside walls of the channels 104 are immersed in the liquid helium contained in the cryogenic dewar 106. The outer and inner ends of each channel 104 are sealed (e.g. welded) to the outer cylindrical wall 110 and inner cylindrical wall 112, respectively, of the cryogenic dewar 106 in order to prevent leakage of liquid helium at these interfaces. As again not shown in diagrammatic FIG. 1, it will be understood that the walls of the channels 104 include any additional thermal isolation structure, such as the already mentioned one or more plenums defining liquid nitrogen and/or vacuum jacketing.

The inner cylindrical wall 112 of the magnet surrounds the examination region 116, sometimes referred to as the bore 116 in the horizontal bore design. Not shown in FIGS. 1 and 2 are other components of a typical MR imaging device, such as cylindrical magnetic field x-, y-, and z-gradient coils. In a typical horizontal bore design, the magnetic field gradient coils are cylindrical components arranged centered on the cylinder axis 100 located coaxially inside the inner cylindrical wall 112 and in some embodiments secured to the inner cylindrical wall 112. (Note that for a horizontal-bore MR imaging device the z-direction is conventionally designated to coincide with the cylinder bore 100, and the x- and y-directions are transverse to each other and to the z-direction). A whole-body radio frequency (RF) coil may also be coaxially arranged inside the inner wall 112 of the magnet, and/or one or more local coils (e.g., head coils, limb coils, torso coils) may be used to generate and/or receive magnetic resonance signals.

As diagrammatically indicated only in FIG. 2, a mechanical rotation system, such as an illustrative motor 118 and gearing (not shown) and cylinder bearing arrangement 119, is provided to controllably rotate the magnet at least over a range sufficient to achieve the desired radiation therapy angular coverage for each channel 104. In the illustrative embodiment with eight channels 104, the mechanical rotation system 118, 119 should provide for the magnet to be rotated at least 360°/8=45° about the cylinder axis 100. It will be appreciated that the appropriate minimum rotation will depend on the number of channels, e.g. if there are only six channels then the mechanical rotation system should provide for the magnet to be rotated at least 360°/6=60° about the cylinder axis 100; whereas, if there are ten channels then the mechanical rotation system should provide for the magnet to be rotated at least 360°/10=36° about the cylinder axis 100. In some embodiments, the rotational angle of the magnet is monitored by an angular position encoder (now shown), such as an optical encoder arranged to read fiduciary marks printed on the magnet bore. Although not shown, it will be appreciated that the mechanical rotation system 118, 119 and optional positional encoder operatively communicate with a radiation therapy controller, e.g. a computer programmed to control the radiation therapy beam delivery apparatus and also the motor 118, to provide synchronization between positioning of the proton beam and the position of the channel 104 currently closest to the beam.

In one embodiment, the annular magnet windings 102, 103 are secured with the cryogenic dewar 106 as a unit, and the mechanical rotation system 118, 119 rotates the dewar 106 and the magnet windings 102, 103 as a unit. While this arrangement is preferred, it is alternatively contemplated to support the annular magnet windings 102, 103 separately from the dewar 106, in which case the mechanical rotation system 118, 119 rotates the dewar 106 while the magnet windings 102, 103 remain stationary.

In another embodiment, the channels have sufficiently large angular spans so that the closed areas between channels are of negligible width. In this case no rotation of the dewar 106 is necessarily, albeit with some loss of angular coverage. In these embodiments, the N channels are widened to an extent that the N zones between channels (comprising radiation-absorbing dewar portions) are small enough to not be too radiation-limiting, so that rotation of the magnet can be avoided altogether. Various "hybrid" designs are also contemplated in which the channels 104 have sufficient angular span to reduce, but not eliminate, the need to rotate the magnet.

In one embodiment, there is only single channel, but in this case to provide full 360° angular coverage for the radiation therapy the dewar 106 may need to be rotated almost a full 360°. Two channels could reduce this to 180° which is easier to achieve, and adding more channels further reduces the requisite angular rotation span (e.g., 8 channels in the illustrative example reduces the angular rotation to 45°. Fewer channels, or even a single channel, may be appropriate if the radiation therapy is to be applied over a smaller angular range, e.g. 180°.

It should be noted that it is advantageous to reduce or eliminate rotation of the magnet because mechanisms in the cryosystem (e.g., a fluid mechanics system) may rely on gravity not changing with respect to their local coordinate system. Thus, one advantage of the techniques disclosed herein is to reduce or eliminate rotation. Another reason that it is desirable to reduce or eliminate rotation is because of issues regarding maintaining a homogeneous magnetic field while rotating.

The disclosed technique is most useful for proton therapy, but also finds use in other forms of radiation therapy such as x-ray radiation therapy or heavy ion therapy. Because protons are electrically charged particles, there will be some beam deflection due to the magnetic field produced by the MR magnet, especially if the proton energy is at the lower end of the therapeutic range. The deflection force can be expressed as $q\bar{v} \times \bar{B}$ where q is the proton charge, $\bar{v}$ is the proton velocity, and $\bar{B}$ is the magnetic field generated by the MR magnet. In some embodiments, the channels are contemplated to be arced or curved, as diagrammatically indicated for one channel in FIG. 2, in accordance with the beam curvature introduced by the $q\bar{v} \times \bar{B}$ force on the protons. The channel diameter may also be controlled to accommodate the beam deflection due to this force.

In proton therapy, the location at which the protons stop is the location at which they deposit most of their energy. And, the depth in the patient that the protons travel (e.g. where the protons deliver the majority of their energy for treatment) is at least partially controlled by the beam energy. For example, a higher energy proton beam will deliver therapy at a greater depth in the patient than a lower energy beam, and this may be used to help target treatment. In addition, patient movement may need to be taken into account when targeting treatment. For example, a patient's breathing and location of ribs may need to be taken into account. Such patient movement may be monitored by the MR imaging.

As previously noted, the channels 104 are air-filled. In this case there will be some beam intensity losses and/or scattering due to proton-air interaction. A variant embodiment includes evacuating the channels 104 (which are then sealed to retain the vacuum) to reduce energy losses/scattering due to proton air interaction. In a similar variant, the sealed channels 104 are back-filled with helium or another gas that has a density less than air. As previously noted, active magnet shim coils may optionally be added that are empirically calibrated for any magnetic field nonuniformity that may be introduced by the different angular positions of the rotated magnet. Another source of design variation is whether the gradient coils and whole body RF coil (if present) are mounted to rotate with the LHe dewar 106. If these components rotate, additional active B1 and/or RF shimming might be added to compensate for rotation of these components. It will also be appreciated that any such components should be arranged respective to the channels 104 in order to avoid having these components interfere with the proton beam.

There is a number of degrees of freedom regarding the relative rotations of magnet and gantry. The maximum magnet rotation angle can be varied depending on the number and size of the channels. Also, the angular velocity functions of the rotating components can be designed to eliminate abrupt motions by choosing smooth, for example using (raised-) cosine-like functions around the stopping positions.

An example distance between magnetic winding sections 102 is 10 cm. Examples of materials used to make the cryostat walls are stainless steel and aluminum, although other materials are contemplated. An example of a proton source is a cyclotron.

Figure 3:
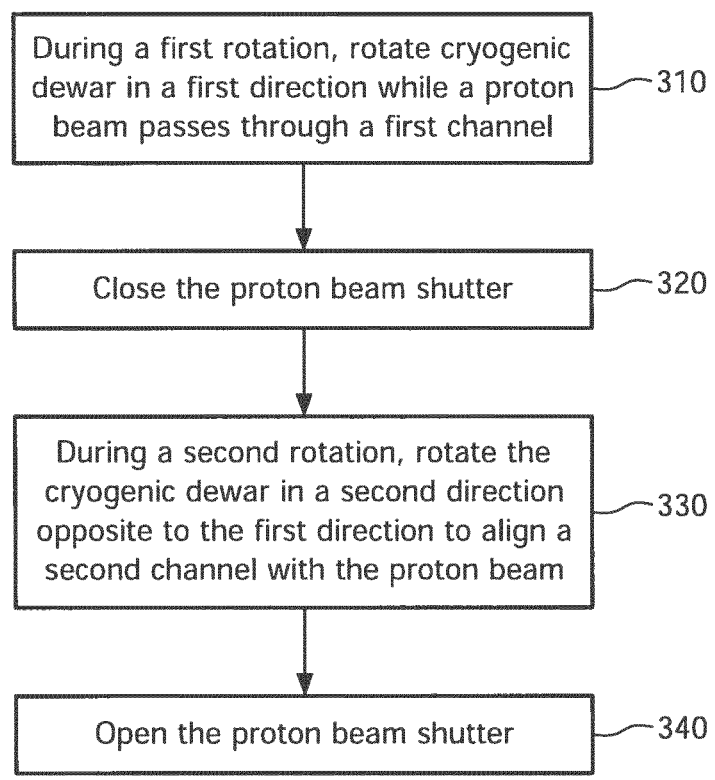
FIG. 3 illustrates an embodiment of a method described herein.

FIG. 3 illustrates an embodiment of a proton therapy method suitably performed using the MR imaging device disclosed herein. With reference thereto, in step 310, during a first rotation, the cryogenic dewar (106) is rotated in a first direction while a proton beam passes through a first channel (104). This can be done in a step-and-shoot mode, e.g. the beam may be stepped in 5° increments with an irradiation scan performed at each incremental angular position. In step 320, a shutter to the proton beam is closed. In step 330, during a second rotation, the cryogenic dewar (106) is rotated in a second direction opposite to the first direction to align a second channel (104) with the proton beam. In step 340, the proton beam shutter is opened so that the proton beam may pass through the second channel (104). It should be noted that steps 310-340 may be repeated such that the proton beam has full 360° access to a target.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A horizontal bore magnet having a cylinder axis, the horizontal bore magnet comprising:
    a cryogenic dewar having an outer cylindrical wall and an inner cylindrical wall arranged coaxially respective to the cylinder axis and a cryogenic fluid plenum defined between the outer and inner cylindrical walls, the inner cylindrical wall surrounding a magnet bore;
    annular magnet windings disposed in the cryogenic fluid plenum; and
    at least one radial channel having an outer end sealed with the outer cylindrical wall of the cryogenic dewar and an inner end sealed with the inner cylindrical wall of the cryogenic dewar, the at least one channel passing radially through the dewar
    wherein the at least one radial channel is curved to account for a $q\bar{v} \times \bar{B}$ force deflecting a proton beam passing through the channel.

2. The horizontal bore magnet of claim 1, wherein the at least one radial channel includes a plurality of radial channels passing radially through the dewar.

3. The horizontal bore magnet according to claim 1, wherein the radial channels are curved to account for the $q\bar{v}\times\bar{B}$ force deflecting a proton beam passing through the channel.

4. The horizontal bore magnet according to claim 1, wherein the cryogenic dewar is a liquid helium dewar, the cryogenic fluid plenum is a liquid helium plenum, and the annular magnet windings are superconducting magnet windings.

5. The horizontal bore magnet according to claim 1, wherein the at least one radial channel is air-filled.

6. The horizontal bore magnet according to claim 1, wherein the at least one radial channel is evacuated of air.

7. The horizontal bore magnet according to claim 1, wherein the at least one radial channel is filled with a gas that has a density less than air, and the at least one radial channel is sealed.

8. The horizontal bore magnet according to claim 1, further comprising a mechanical rotation system comprising a motor arranged to rotate the dewar about the cylinder axis over an angle of at least 360°/N where N is the number of channels.

9. The horizontal bore magnet according to claim 8, wherein one of:
the annular magnet windings are secured with the cryogenic dewar as a unit and the mechanical rotation system rotates the annular magnet windings and the cryogenic dewar as a unit; and
the annular magnet windings are supported separately from the cryogenic dewar and the mechanical rotation system rotates the cryogenic dewar while the annular magnet windings remain stationary.

10. The horizontal bore magnet according to claim 1, wherein a cosine function is used to smooth a stopping of rotation of the dewar.

11. A magnetic resonance (MR) imaging system, comprising:
a horizontal bore magnet including a cryogenic dewar having multiple channels passing through the dewar towards a cylinder axis of the cryogenic dewar
a mechanical rotation system configured to rotate the dewar.

12. The MR imaging system according to claim 11, wherein the mechanical rotation system is programmed to control rotation of the dewar such that the dewar rotates synchronously with a proton beam tomographically revolving around the cylinder axis.

13. The MR imaging system according to claim 12, wherein the channels are curved in accordance with a $q\bar{v}\times\bar{B}$ force on protons.

14. The MR imaging system according to claim 11, wherein the channels are air-filled channels.

15. The MR imaging system according to claim 11, wherein the channels are filled with a gas that has a density less than air, and the channels are sealed.

16. A method of magnetic resonance (MR) imaging performed in conjunction with an MR device including magnet windings generating a magnetic field for MR imaging and a cryogenic dewar containing the magnet windings, the cryogenic dewar including at least one channel passing radially through the cryogenic dewar, the method comprising:
during a first rotation, rotating, in a first direction, the cryogenic dewar while a proton beam passes through a first channel of the cryogenic dewar towards a center axis of the dewar.

17. The method of claim 16, further comprising:
during a second rotation performed after completing the first rotation, rotating, in a second direction opposite to the first direction, the cryogenic dewar to align a second channel of the dewar with the proton beam.

18. The method according to claim 16, wherein the magnetic windings are secured with the cryogenic dewar such that the rotating rotates the cryogenic dewar and the magnetic windings together as a unit.

19. The method according to claim 16, wherein the first rotating is performed in a step-and-shoot operation in which the proton beam is stepped in increments with an irradiation scan performed at each incremental angular position.

* * * * *